(12) United States Patent
Roberts et al.

(10) Patent No.: US 9,352,099 B2
(45) Date of Patent: May 31, 2016

(54) SAFETY DEVICE FOR A PRE-FILLED SYRINGE AND INJECTION DEVICE

(75) Inventors: Gareth Roberts, Wrexhan (GB); Chris Ward, Prestatyn (GB); Matthew Ekman, Macclesfield (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 596 days.

(21) Appl. No.: 13/808,084

(22) PCT Filed: Jun. 21, 2011

(86) PCT No.: PCT/EP2011/060319
§ 371 (c)(1),
(2), (4) Date: Aug. 7, 2013

(87) PCT Pub. No.: WO2012/000835
PCT Pub. Date: Jan. 5, 2012

(65) Prior Publication Data
US 2013/0324923 A1   Dec. 5, 2013

(30) Foreign Application Priority Data

Jul. 2, 2010   (EP) ..................................... 10168317

(51) Int. Cl.
*A61M 5/32*   (2006.01)
*A61M 5/28*   (2006.01)

(52) U.S. Cl.
CPC ............. *A61M 5/3204* (2013.01); *A61M 5/326* (2013.01); *A61M 5/3272* (2013.01); *A61M 5/28* (2013.01); *A61M 2005/3267* (2013.01)

(58) Field of Classification Search
CPC ............ A61M 5/3271; A61M 5/3272; A61M 2005/3267

USPC ..................................... 604/164.08, 192, 198
See application file for complete search history.

(56) References Cited

U.S. PATENT DOCUMENTS 4,966,592 A * 10/1990 Burns ................. A61M 5/3271
                                                          604/198
4,988,339 A *  1/1991 Vadher .................. A61M 5/326
                                                          604/117

(Continued)

FOREIGN PATENT DOCUMENTS

WO        2009040602 A1   4/2009
WO        2010019936 A1   2/2010

OTHER PUBLICATIONS

Form PCT/IB/326, Notification Concerning Transmittal of International Preliminary Report on Patentability.

*Primary Examiner* — Gerald Landry, II
(74) *Attorney, Agent, or Firm* — Fish & Richardson P.C.

(57) ABSTRACT

According to the invention, a safety device for a pre-filled syringe comprises a hollow support body for mounting the pre-filled syringe therein, a hollow needle shield that is slidable relative to the support body and guiding means for guiding the movement of the needle shield relative to the support body. The guiding means comprise a flexible arm with a guide pin, a guide track and a separating wall. The guide pin extends from the flexible arm in a radial direction, and protrudes into the guide track. The separating wall extends into the guide track in a direction parallel to a central axis of the safety device. When the needle shield is slid relative to the support body the guide pin moves along the guide track to deflect the flexible arm in a lateral direction perpendicular to the central axis and the movement of the guide pin along the guide track is guided by the interplay of the flexible arm and the separating wall.

19 Claims, 5 Drawing Sheets (56) References Cited

U.S. PATENT DOCUMENTS

| | | | |
|---|---|---|---|
| 6,830,560 B1 | 12/2004 | Gross et al. | |
| 6,884,237 B2 * | 4/2005 | Asbaghi | A61M 5/3272 604/192 |
| 2003/0144630 A1 * | 7/2003 | Chang | A61M 5/3272 604/198 |
| 2004/0111064 A1 * | 6/2004 | Asbaghi | A61M 5/3272 604/198 |
| 2006/0189933 A1 * | 8/2006 | Alheidt | A61M 5/326 604/110 |
| 2006/0282044 A1 * | 12/2006 | Mohammed | A61B 5/1444 604/192 |
| 2008/0109025 A1 * | 5/2008 | Yang | A61B 5/15142 606/182 |
| 2008/0228147 A1 * | 9/2008 | David-Hegerich | A61M 5/326 604/198 |
| 2008/0262436 A1 * | 10/2008 | Olson | A61M 5/2033 604/198 |
| 2009/0024093 A1 * | 1/2009 | Carrel | A61M 5/326 604/198 |
| 2009/0259178 A1 * | 10/2009 | Brechbuehler | A61M 5/326 604/110 |
| 2011/0319832 A1 * | 12/2011 | Chun | A61M 5/326 604/198 |

* cited by examiner

SAFETY DEVICE FOR A PRE-FILLED SYRINGE AND INJECTION DEVICE

CROSS REFERENCE TO RELATED APPLICATIONS

The present application is a U.S. National Phase Application pursuant to 35 U.S.C. §371 of International Application No. PCT/EP2011/060319 filed Jun. 21, 2011, which claims priority to European Patent Application No. 10168317.5 filed Jul. 2, 2010. The entire disclosure contents of these applications are herewith incorporated by reference into the present application.

FIELD OF INVENTION

The present invention relates to safety devices that provide needle safety and more particularly to safety devices for pre-filled syringes. The safety device is adapted to avoid accidental needle pricks and needle injuries before, during and after an injection of a medication or drug contained in the pre-filled syringe. In particular, the safety device provides needle safety for a subcutaneous self-administrated injection or for an injection administered by a health-care professional. The present invention further relates to injection devices comprising a pre-filled syringe.

BACKGROUND

Pre-filled syringes that are filled with a selected dosage of a medication are well known injection devices for administering the medication to a patient. Safety devices for covering a needle of a pre-filled syringe before and after use are also well known. Typically, these devices comprise a needle shield that is either manually moved or moved by the action of a relaxing spring to surround the needle.

A different type of safety devices known in the state of the art solve the object of providing needle safety by arranging the pre-filled syringe movable relative to a body, whereas the pre-filled syringe is retracted into the body after the injection.

SUMMARY

It is an object of the present invention to provide an improved safety device for a pre-filled syringe.

It is a further object of the invention to provide an improved injection device comprising a pre-filled syringe that is safe to handle and in particular prevents accidental needle stick injuries.

The object is achieved by a safety device according to claim 1 and by an injection device according to claim 17.

Preferred embodiments of the invention are given in the dependent claims.

In the context of this specification, the terms distal and proximal are defined from the point of view of a person performing an injection. Consequently, a distal direction refers to a direction pointing towards the body of a patient receiving an injection and a distal end defines an end of an element that is directed towards the body of the patient. Respectively, the proximal end of an element or the proximal direction is directed away from the body of the patient receiving the injection and opposite to the distal end or distal direction.

According to the invention, a safety device for a pre-filled syringe comprises a hollow support body for mounting the pre-filled syringe therein, a hollow needle shield that is slidable relative to the support body and guiding means for guiding the movement of the needle shield relative to the support body. The guiding means comprise a flexible arm, a guide track and a separating wall. A guide pin extends from the flexible arm in a radial direction and protrudes into the guide track. The separating wall extends into the guide track in a direction parallel to a central axis of the safety device. When the needle shield is slid relative to the support body the guide pin moves along the guide track to deflect the flexible arm in a lateral direction perpendicular to the central axis and the movement of the guide pin along the guide track is guided by the interplay of the flexible arm and the separating wall.

The guide pin is moved within and along the guide track when the needle shield is slid relative to the support body to cover and/or to expose in particular a hypodermic needle of a pre-filled syringe inserted into the support body of the safety device. The movement of the needle shield is controlled by the guide pin moving between various positions within the guide track. The interplay of the deflectable flexible arm with the separating wall allows a guidance of the guide pin along the guide track that avoids a relative rotation of any external parts like the needle shield and the support body. Especially when external parts of the safety device abut the skin of a patient during the injection, friction between these rotating external parts and the skin of the patient is uncomfortable and may even cause pain to the patient, in particular while a hypodermic needle of the pre-filled syringe still penetrates the skin. The safety device thus allows for a safe and convenient injection of a medication.

The flexible arm is connected to either the needle shield or the support body. The guide track is formed into the other of the needle shield or the support body. Therefore, it is within the scope of the present invention that the safety device comprises the support body with the guide track and the needle shield with the flexible arm, or, alternatively, that the flexible arm is connected to the support body and the guide track is formed into the needle shield. The separating wall extends into a widened section of the guide track that extends parallel to the central axis of the safety device. The separating wall together with the flexible arm provide an efficient mechanism that guides the movement of the guide pin with the guide track, whereby the guide pin is prevented to re-enter a start position and guided towards an end position. The guide pin in the end position permanently retains the needle shield in an advanced position, whereas the needle shield protrudes the support body to surround the hypodermic needle of the pre-filled syringe retained in the support body. The separating wall is a means that prevents a re-exposure of the hypodermic needle after a single use of the safety device, so that accidental needle stick injuries in particular with contaminated needles are prevented.

As soon as the guide pin passes the separating wall, the safety device is prevented from re-usage. The separating wall has an axial dimension extending parallel to the central axis that substantially defines a minimal axial distance that the needle shield has to be moved with respect to the support body in the proximal direction until the guide pin is allowed to pass the flexible wall to prevent the re-usage of the safety device. If the needle shield is inadvertently pushed in the proximal direction by an axial length less than the axial dimension of the flexible wall, the safety features that in particular prevent the re-usage are not activated. Thus, an accidental activation of the safety features preventing the re-usage of the safety device is avoided.

According to a possible embodiment of the invention, an audible feedback is generated when the needle shield is retracted with respect to the support body by a distance that matches or exceeds the minimal axial distance. This indicates the user of the safety device the activation of the safety features that prevent accidental needle stick injuries and re-usage after a single injection has been performed.

The separating wall prevents the guide pin to access the end position from one of the distal direction or the proximal direction, whereas the guide pin is allowed to enter the end position from the other of the distal direction or the proximal direction. The separating wall provides a means that requires the needle shield to be retracted to expose the hypodermic needle before the end position is accessible for the guide pin to enter.

According to alternative embodiments, the separating wall is either static or flexible and deflectable.

According to possible embodiments of the invention, the guide track is formed either into a surface of the support body or into a surface of the needle shield as a recess. The guide track does not completely pass through a wall of the corresponding part into which the guide track is formed. According to possible embodiments, this corresponding part may be the needle shield or the support body. This ensures that there is no direct access from the outside of the safety device to the inside and thus increases the robustness of the safety device. Additionally, the structural stability of the part having the guide track is increased. As the support body and the needle shield are preferably formed by a process of injection moulding, the guide track shaped as a recess additionally eliminates a moulding defect known as flash along the guide track. Flash is occurs when excess material exceeds the normal part geometry. Thus, as the guide track has the shape of a recess, flash is avoided and the smoothness of the guide track is increased.

According to an alternative embodiment, the guide track forms an aperture into either the support body or the needle shield. This allows the separating wall to be flexible and deflectable in the lateral direction.

According to the same embodiment of the invention, the deflection of the flexible separating wall depends on the deflection of the flexible arm supporting the guide pin. The dependant interplay of the flexible arm and the flexible separating wall reduces a degree of the deflection required from the flexible arm to safely guide the guide pin along the guide track. Additionally, the dependant interplay reduces an amount of time that the flexible arm is required to be in its maximum stressed state. Therefore, an input force exerted upon the safety device to move the needle shield relative to the support body by a user is reduced.

According to the same embodiment, an elasticity of the flexible separating wall is adapted to an elasticity of the flexible arm, so that the flexible separating wall is deflectable by the deflected and stressed flexible arm. The amount of work done to deflect the flexible arm by the user is substantially transferred to the flexible separating wall to deflect said flexible wall. Advantageously, the flexible separating wall and the flexible arm are made from the same resilient plastics material or from different plastics materials substantially having the same elasticity.

The guide pin is biased in the lateral direction by the deflected flexible arm. According to one embodiment of the invention, the biased guide pin exerts a force in the lateral direction upon the flexible separating wall to deflect the separating wall, so that the safety features of the safety device are activated. According to another embodiment of the invention, the guide pin is biased by the flexible arm to pass the separating wall in the lateral direction.

The flexible arm in a rest position extends essentially parallel to the central axis. The safety device is stored with the flexible arm in its rest position and stressed during the first single use of the safety device. As the flexible arm is a biasing means typically made from a resilient plastics material that is prone to material fatigue, it is advantageous to avoid storing the flexible arm in a stressed state in order to extend the shelf-life of the safety device.

The guide track comprises an inclined section oriented at an angle with respect to the central axis. When the guide pin moves along the inclined section of the guide track, the flexible arm is deflected and thus stressed. The design of the guide track thus allows for an energizing of the flexible arm during use of the safety device to avoid fatigue of material. Needle safety is thus reliably provided even after periods of storage.

The needle shield is retained in an initial position by the guide pin being retained in the start position within the inclined section of the guide track. The needle shield in the initial position protrudes the support body in a distal direction.

According to a possible embodiment, the needle shield is made from an opaque plastics material. The hypodermic needle is hidden from the view of the patient before the injection by the needle shield that is retained in the initial position. This eases a possible fear of needles of the patient. The safety device is thus particularly suited for performing self-administered injections.

According to an alternative embodiment, the needle shield is made from a transparent plastics material. A healthcare professional that uses the safety device thus can visually confirm the correct placement of the hypodermic needle penetrating the skin of the patient, even when the hypodermic needle is surrounded by the needle shield.

As the safety device is both suited for self-administered injections and injections carried out by a healthcare professional, the person referred to as the user or the patient may be one and the same person.

A compression spring is arranged in a non-energized state when the needle shield is in the initial position. As the safety device is stored and transported with the needle shield retained in the initial position, a fatigue of material of the compression spring is avoided. The shelf-life of the safety device is thus extended. Furthermore, the requirements for the material of the compression spring are low, so that the safety device can be cost-efficiently mass-produced.

The needle shield is movable from the initial position to a retracted position and further to the advanced position. The needle shield protrudes the support body in the initial position. The needle shield in the retracted position is substantially received in the support body.

Alternatively, the substantial cylindrical needle shield comprises a radial diameter that is sized to substantially receive the support body in the retracted position. In this alternative embodiment the support body slides into the needle shield when the needle shield is moved from the advanced to the retracted position.

In the advanced position, the needle shield extends from the support body in the distal direction. The movement of the guide pin within and along the guide track controls the extension and retraction of the needle shield allowing for a safe injection.

An injection device comprises a pre-filled syringe retained in the support body of the safety device. The pre-filled syringe comprises a hypodermic needle attached to a distal end of the pre-filled syringe, a barrel with an inner cavity in fluid communication with the hypodermic needle and a piston fluid-tightly sealing a proximal end of the inner cavity. The piston is movable by actuating a piston rod protruding a proximal end of the barrel. The pre-filled syringe is retained within the support body of the safety device, so that the hypodermic needle protrudes the distal end of the support body. The hypodermic needle of the injection device is surrounded by the needle shield in the initial position and in the advanced position and the hypodermic needle is exposed when the needle shield is in the retracted position. The injection device comprising the pre-filled syringe and the safety device combines the aforementioned advantages and avoids inadvertent needle sticks before, during and after an injection delivering the medication beneath the skin of patient.

Details of the present invention are described hereinafter. However, it should be understood that the detailed description and the specific examples indicate possible embodiments of the invention and are given by way of illustration only. Various changes and modifications of the illustrated embodiments within the spirit and scope of the invention are appreciated by those skilled in the art.

BRIEF DESCRIPTION OF THE DRAWINGS

The present invention will be better understood from the detailed description given in the following. The accompanying drawings are given for illustrative purposes only and do not limit the scope of the present invention.

Corresponding parts are marked with the same reference symbols in all figures.

DETAILED DESCRIPTION

Figure 1:
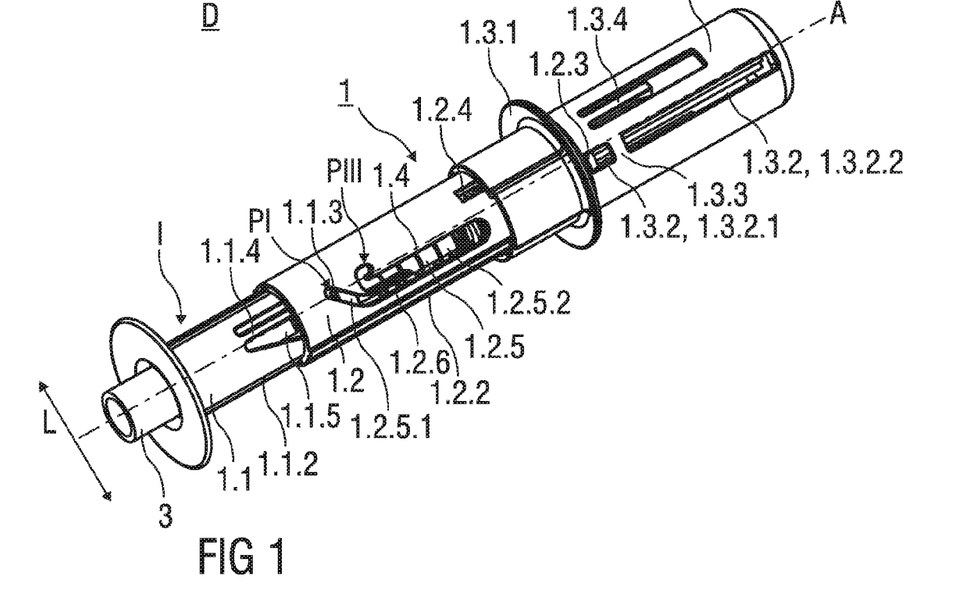
FIG. 1 shows a perspective view of an injection device according to a first embodiment of the invention prior to use comprising a safety device and a pre-filled syringe.

FIG. 1 shows an injection device D with a safety device 1 for a pre-filled syringe 2 according to a first embodiment of the invention as it would be presented to a user performing an injection. The safety device 1 comprises a substantially cylindrical and hollow needle shield 1.1. The needle shield 1.1 is received within a substantially cylindrical and hollow support body 1.2, whereas the needle shield 1.1 is slidable with respect to the support body 1.2. Prior use of the safety device 1, the needle shield 1.1 is retained in an initial position I, wherein the needle shield 1.1 protrudes the support body 1.2.

Alternatively, the needle shield 1.1 comprises a radial diameter that is sized to substantially receive the support body 1.2. In this alternative embodiment the support body 1.2 slides into the needle shield 1.1 when the needle shield 1.1 is moved from the initial position I to a refracted position II.

FIG. 1 shows the safety device 1 that comprises an essentially cylindrical and hollow outer body 1.3 with an open distal and a closed proximal end. The proximal end of the support body 1.2 is received within the open distal end of the outer body 1.3, whereas the outer body 1.3 is slidable with respect to the support body 1.2 in a distal direction to substantially receive the support body 1.2 inside the outer body 1.3.

A circumferential and outwardly protruding hand flange 1.3.1 is integrally formed to an outer surface of the outer body 1.3 close to its distal end.

Preferably, the needle shield 1.1, the support body 1.2 and the outer body 1.3 are made from a plastics material.

The needle shield 1.1 comprises a circumferential skin-contact surface 1.1.1 at its distal end. The skin-contact surface 1.1.1 is adapted to be pressed against the skin of a patient and protrudes radial outwardly and perpendicular to a central axis A of the safety device 1. Edges of the skin-contact surface 1.1.1 that come into contact with the skin of the patient are rounded to avoid injuries. The skin-contact surface 1.1.1 has a central opening centred on the central axis A of the safety device 1. The skin-contact surface 1.1.1 is integral to the needle shield 1.1, or alternatively, a separate part attached to the needle shield 1.1 that is made from a plastics material.

Figure 2:
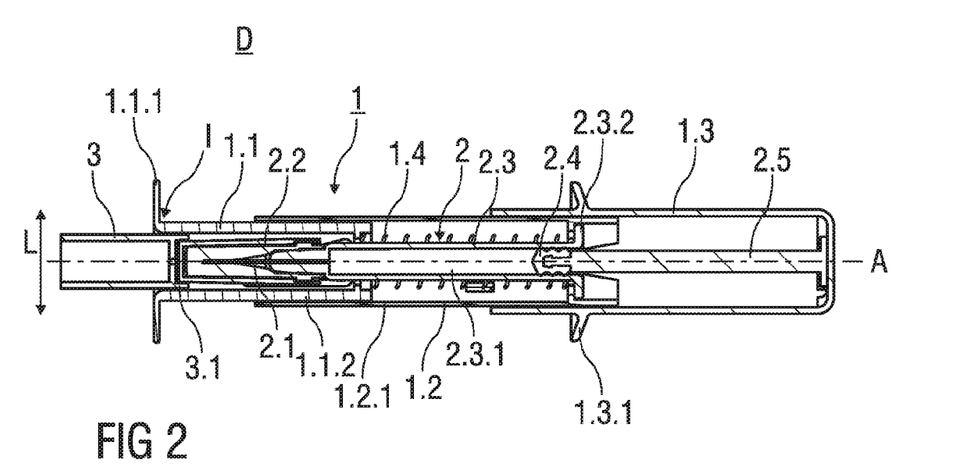
FIG. 2 shows a sectional view of the injection device according to the first embodiment of the invention with the safety device comprising a needle shield retained in an initial position.

Two diametrical opposing first longitudinal tongues 1.1.2 are formed to an outer surface of opposite sides of the needle shield 1.1. Each first longitudinal tongue 1.1.2 protrudes radial outwardly and extends over an axial length parallel to a central axis A of the needle shield 1.1. As best seen in FIG. 2, the first longitudinal tongue 1.1.2 is received in a corresponding first longitudinal groove 1.2.1 formed into an inner surface of the support body 1.2. A relative rotation of the support body 1.2 and the needle shield 1.1 is prevented by the first longitudinal groove 1.2.1 receiving the first longitudinal tongue 1.1.2 of the needle shield 1.1.

Correspondingly, the support body 1.2 comprises at least one second longitudinal tongue 1.2.2 that is received in a second longitudinal groove (not illustrated) formed into an inner surface of the outer body 1.3, whereby a relative rotation of outer body 1.3 and support body 1.2 is prevented.

Two longitudinal recesses 1.3.2 are formed into the opposite sides of the outer body 1.3 that extend over a substantial axial length of the outer body 1.3 and parallel to the central axis A. The longitudinal recess 1.3.2 comprises two sections, a first section 1.3.2.1 and a second section 1.3.2.2 separated from each other by a web 1.3.3.

Each longitudinal recess 1.3.2 receives a corresponding outward projection 1.2.3 being integral to the support body 1.2. The outward projection 1.2.3 moves within the longitudinal recess 1.3.2 when the outer body 1.3 is slid relative to the support body 1.2 to perform the injection stroke, whereas a rotation of the outer body 1.3 relative to the support body 1.2 is prevented.

Prior the injection, the outward projection 1.2.3 is retained in the first section 1.3.2.1 of the longitudinal recess 1.3.2. The outward projection 1.2.3 is deflectable in a radial inward direction, so that the outward projection 1.2.3 leaves the first section 1.3.2.1 and enters the second section 1.3.2.2 when the outer body 1.3 is pushed with respect to the support body 1.2 in the distal direction. The shape and elasticity of the outward projection 1.2.3 and the first section 1.3.2.1 of the longitudinal recess 1.3.2 are adjusted in a manner that a force, required for the outward projection 1.2.3 to leave the first section 1.3.2.1, exceeds a force required to move the needle shield 1.1 from the initial position I to the retracted position II. This ensures a stage-wise movement of the needle shield 1.1, the support body 1.2 and the outer body 1.3 during the injection as described in more detail herein below.

The longitudinal recess 1.3.2 shown in FIG. 1 has the form of a slot. Alternatively, the longitudinal recess 1.3.2 is formed into an inner surface of the outer body 1.3, so that the outward projection 1.2.3 moves along the longitudinal recess 1.3.2 within the outer body 1.3 and is inaccessible from the outside.

Figure 5:
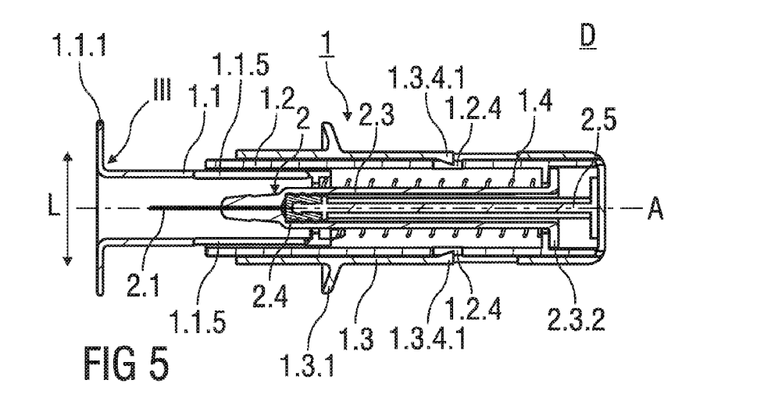
FIG. 5 shows a sectional view of the injection device according to the first embodiment of the invention after an injection has been performed.

A clamp arm 1.3.4 is formed into the substantially cylindrical outer body 1.3 that is deflectable in the radial direction perpendicular to the central axis A. As best seen in FIG. 5, the clamp arm 1.3.4 comprises an inwardly protruding locking catch 1.3.4.1 that is sized to fit into a locking recess 1.2.4 formed into the support body 1.2 in proximity of a proximal end of the support body 1.2.

A guide pin 1.1.3 is integrally formed to a flexible arm 1.1.4 of the needle shield 1.1. The flexible arm 1.1.4 extends in its rest position essentially parallel to the central axis A of the safety device 1. As illustrated in FIG. 1, the guide pin 1.1.3 protrudes radial outwards into a guide track 1.2.5 formed into the substantially cylindrical support body 1.2 as an aperture. A trapezoid cut-out 1.1.5 is formed into the needle shield 1.1 adjacent to the flexible arm 1.1.4 to allow for a deflection and pivoting movement of the flexible arm 1.1.4. Prior to use of the safety device 1, the guide pin 1.1.3 is retained within an inclined section 1.2.5.1 of the guide track 1.2.5 in a start position PI located at a distal end of the guide track 1.2.5. As the flexible arm 1.1.4 is in the rest position, the guide pin 1.1.3 is laterally non-biased in the start position PI. The inclined section 1.2.5.1 is oriented at an acute angle relative to the cylindrical axis A of the safety device 1.

The needle shield 1.1 is retained in an initial position I by the guide pin 1.1.3 being retained in a start position PI in the inclined section 1.2.5.1 of the guide track 1.2.5. The needle shield 1.1 is made from an opaque plastics material, so that the hypodermic needle 2.1 is hidden from view of the patient before the injection.

Alternatively, the needle shield 1.1 is made from a transparent plastics material, so that a healthcare professional performing the injection may visually confirm the correct placement of the hypodermic needle 2.1 before penetrating the skin of the patient.

The guide pin 1.1.3 is prevented from leaving the start position PI by an interaction of several components of the safety device 1: The flexible arm 1.1.4 biases the guide pin 1.1.3 in the lateral direction L, the guide pin 1.1.3 abuts the distal end of the inclined section 1.2.5.1 in the lateral direction L and distal direction and a compression spring 1.4, as best seen in FIG. 2, is arranged between the support body 1.2 and the needle shield 1.1, so that the needle shield 1.1 and the guide pin 1.1.3 connected thereto are biased in the distal direction.

The guide track 1.2.5 comprises a widened section 1.2.5.2 extending parallel to the central axis A of the safety device 1. A separating wall 1.2.6 extends parallel to the central axis A and into the widened section 1.2.5.2 from a distal direction. The separating wall 1.2.6 is integral to the support body 1.2 and acts as a no-return feature preventing the guide pin 1.1.3 from returning to its start position PI after an injection stroke has been carried out. Furthermore, the separating wall 1.2.6 guides the movement of the guide pin 1.1.3 within the guide track 1.2.5, so that the guide pin 1.1.3 is prevented to enter an end position PIII from the distal direction but allowed to enter from the proximal direction. The end position PIII is defined by a generally U-shaped indent between the distal and a proximal end of the guide track 1.2.5.

According to the first embodiment of the invention shown in FIGS. 1 to 6F, the separating wall 1.2.6 is flexible and deflectable in lateral direction L.

The injection device D comprises the safety device 1 with the pre-filled syringe 2 retained within the support body 1.2. FIG. 2 shows the pre-filled syringe 2 received within the support body 1.2 that comprises a hypodermic needle 2.1 covered by a needle cap 2.2 frictionally affixed to a distal end of a barrel 2.3. The barrel 2.3 has an inner cavity 2.3.1 containing a medication. The inner cavity 2.3.1 is in fluid communication with the hypodermic needle 2.1. A proximal end of the inner cavity 2.3.1 is fluid-tightly sealed by a piston 2.4 that is connected to a piston rod 2.5. The piston 2.4 is movable in at least the distal direction by actuating the piston rod 2.5 protruding the barrel 2.3 in the proximal direction. The barrel 2.3 of the pre-filled syringe 2 comprises a barrel collar 2.3.2 that abuts a radial inwardly protruding inner surface of the support body 1.2 at its proximal end affixing the pre-filled syringe 2 to the support body 1.2.

Figure 4:
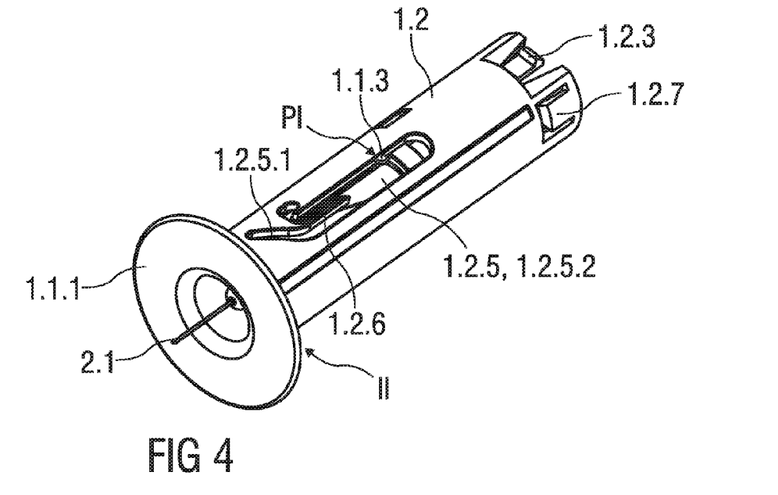
FIG. 4 shows a perspective view of a support body and a needle shield of a safety device, whereas the needle shield is retained in a retracted position.

With cross-reference to FIG. 4, it can be seen that the support body 1.2 comprises clips 1.2.7 that engage the barrel collar 2.3.2 to retain the pre-filled syringe 2 within the support body 1.2.

The pre-filled syringe 2 is retained within the support body 1.2, whereby the hypodermic needle 2.1 protrudes the support body 1.2 in the distal direction.

In the packaged state as shown in FIGS. 1 and 2, the hypodermic needle 2.1 is covered by a needle cap 2.2 that is surrounded by the needle shield 1.1 prior to use of the injection device D. The needle cap 2.2 is preferably at least partially made from a plastics material like rubber. The width of the central opening of the skin-contact surface 1.1.1 corresponds to an outer diameter of the needle cap 2.2. A needle cap remover 3 is inserted into the central opening of the skin-contact surface 1.1.1 and protrudes the skin-contact surface 1.1.1 in a distal direction, so that the user can easily remove the needle cap 2.2 from the pre-filled syringe 2 by pulling the needle cap remover 3 in the distal direction. The needle cap remover 3 comprises clamp means 3.1 that clamp to a distal end of the needle cap 2.2.

Alternatively, the injection device D comprising the safety device 1 with the pre-filled syringe 2 retained therein is shipped and delivered to an end-user with a needle cap remover 3 attached to the distal end of the needle cap 2.2 retained within the safety device 1, so that the needle cap remover 3 protrudes the needle shield 1.1 in the distal direction.

A proximal end of the piston rod 2.5 abuts the closed distal end of the outer body 1.3, so that the piston 2.4 is movable in a distal direction by the distal displacement of the outer body 1.3 with respect to the support body 1.2.

Alternatively, the piston rod 2.5 is connected to the outer body 1.3 or an integral part of the outer body 1.3. This alternative embodiment has additional advantage of a low overall part count, so that manufacturing costs are reduced.

The needle shield 1.1 is in the initial position I surrounding the hypodermic needle 2.1 of the pre-filled syringe 2. The compression spring 1.4 is arranged within the safety device 1 in a partially energized state distally bearing against an inner surface of the needle shield 1.1 and proximally bearing against an inner surface of the support body 1.2, thereby biasing these two parts 1.1, 1.2 away from each other. The needle shield 1.1 is retained in the initial position I by the guide pin 1.1.3 abutting against the support body 1.2 in the start position PI.

Figure 3:
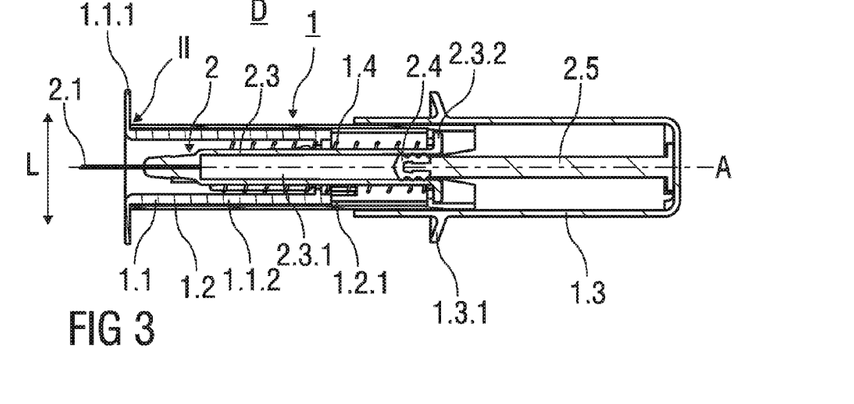
FIG. 3 shows a sectional view of the injection device according to the first embodiment of the invention with the safety device with the needle shield retained in a retracted position.

FIG. 3 shows a sectional view of the needle shield 1.1 in the retracted position II, wherein the needle shield 1.1 is substantially received within the support body 1.2. The hypodermic needle 2.1 distally protrudes the skin-contact surface 1.1.1 of the needle shield 1.1. The compression spring 1.4 that is arranged within the safety device 1 is fully compressed and thus fully energized.

FIG. 4 shows a perspective view of the needle shield 1.1 in a retracted position II, wherein the needle shield 1.1 is substantially received within the support body 1.2. The guide pin 1.1.3, that is integral part of the needle shield 1.1 is in an intermediate position PII within the guide track 1.2.5 and in proximity of a proximal end thereof. The intermediate position PI corresponds to the retracted position II of the needle shield 1.1.

The support body 1.2 further comprises two clips 1.2.7 arranged diametrical opposite to each other. The clips 1.2.7 are located near the proximal end of the support body 1.2 and clamp to the collar 2.3.2 of the pre-filled syringe 2 to affix the pre-filled syringe 2 to the support body 1.2, so that the pre-filled syringe 2 is firmly retained within the support body 1.2.

FIG. 5 shows a sectional view the injection device D according to the first embodiment of the invention after the injection of the medication. The sectional view given in FIG. 5 is rotated with respect to the sectional views shown in FIGS. 2 and 3 about an angle of 90 degrees around the central axis A. The needle shield 1.1 is in an advanced position III distally protruding from the support body 1.2, whereas the hypodermic needle 2.1 is surrounded by the needle shield 1.1 to avoid accidental needle stick injuries. The needle shield 1.1 is fixed to the advanced position III by the guide pin 1.1.3 being retained in the end position PIII.

The piston 2.4 is fully depressed inside the barrel 2.3 of the pre-filled syringe 2. The support body 1.2 is received within the outer body 1.3 and locked to it, so that a re-usage of the safety device 1 is prevented. The inwardly protruding locking catch 1.3.4.1 formed to the clamp arm 1.3.4 latches to the corresponding locking recess 1.2.4 formed into the support body 1.2 to irreversibly lock the support body 1.2 with respect to the outer body 1.3.

FIGS. 6A to 6F show details of the guide track 1.2.5 formed into the support body 1.2 and the movement of the guide pin 1.1.3 within the guide track 1.2.5 during use of the safety device 1 according to the first embodiment. FIGS. 6A to 6F illustrate the dependant interaction of the flexible arm 1.1.4 with the flexible and deflectable separating wall 1.2.6.

Figure 6A:
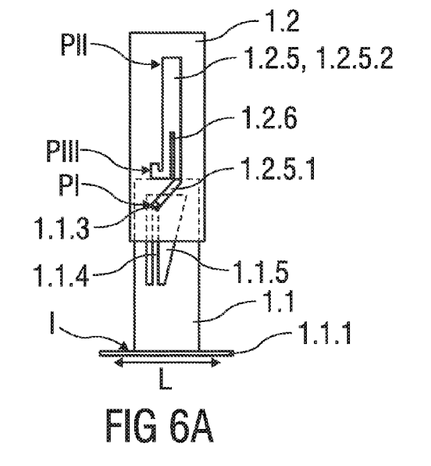
FIGS. 6A to 6F show details of a guide track and the movement of a guide pin within the guide track during use of the safety device according to the first embodiment of the invention.

As shown in FIG. 6A, the guide pin 1.1.3 is retained prior to the injection in the start position PI at the distal end of the inclined section 1.2.5.1 of the guide track 1.2.5, affixing the needle shield 1.1 to the initial position I. In the initial position I, the hypodermic needle 2.1 is surrounded by the needle shield 1.1.

The injection is carried out by orientating the central axis A essentially perpendicular to the skin of the patient, whereas the skin-contact surface 1.1.1 of the needle shield 1.1 rests on the skin surface of the patient and the proximal section of the outer body 1.3 proximal of the hand flange 1.3.1 is gripped by the user performing the injection. The hand flange 1.3.1 supports the hand of the user to carry out an injection stroke, whereby the outer body 1.3 is distally moved towards the skin surface of the patient to initiate the injection.

Figure 6B:
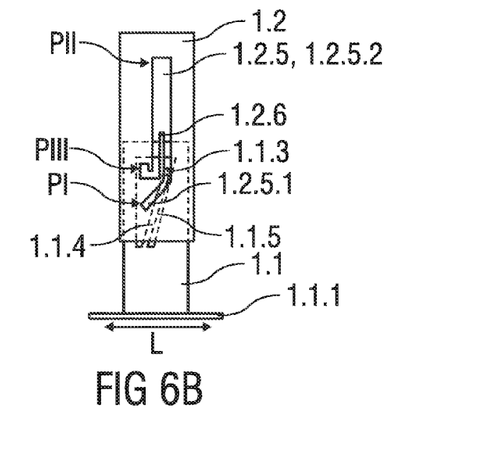

The injection is carried out in stages. In a first stage, the needle shield 1.1 is pushed inside the support body 1.2 in the proximal direction against the biasing force of the compression spring 1.4. As illustrated in FIG. 6B, the guide pin 1.1.3 leaves its start position PI and moves along the inclined section 1.2.5.1 of the guide track 1.2.5. As the distal end section 1.2.5.1 is oriented at an acute angle relative to the central axis A, the movement of the guide pin 1.1.3 causes the flexible arm 1.1.4 to become laterally deflected and stressed, so that the guide pin 1.1.3 is biased in a lateral direction.

Figure 6C:
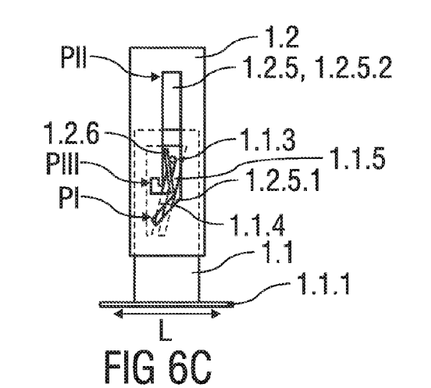

The guide pin 1.1.3 travels further along the guide track 1.2.5 in the proximal direction. As shown in FIG. 6C, the guide pin 1.1.3 enters the widened section 1.2.5.2 of the guide track 1.2.5 and abuts the flexible separating wall 1.2.6 in the lateral direction. The flexible separating wall 1.2.6 is laterally deflected by a force exerted upon the flexible separating wall 1.2.6 by the stressed flexible arm 1.1.4. The elasticity of the flexible separating wall 1.2.6 is adapted to correspond to the elasticity of the flexible arm 1.1.4, so that the flexible separating wall 1.2.6 is deflectable by the deflected and stressed flexible arm 1.1.4.

The separating wall 1.2.6 prevents the guide pin 1.1.3 from entering the end position PIII as the guide pin 1.1.3 enters the widened section 1.2.5.2 from the distal direction.

Figure 6D:
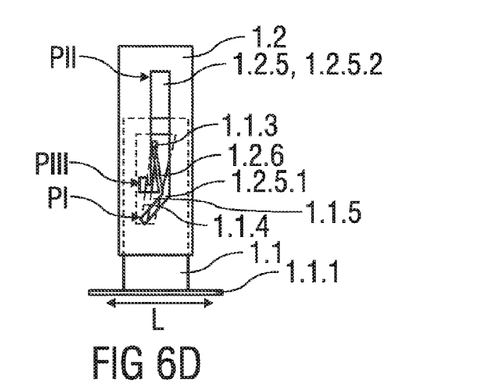

The guide pin 1.1.3 moves further proximally towards an intermediate position PII and reaches a proximal end of the flexible separating wall 1.2.6, as illustrated in FIG. 6D. At this point, the safety features of the safety device 1 are activated, as the flexible separating wall 1.2.6 relaxes and snaps back into its rest position substantially parallel to the central axis A. From now on, the end position PIII is accessible for the guide pin 1.1.3 to enter whereas the guide pin 1.1.3 is prevented to re-enter the start position PI. A removal of the safety device 1 would cause the needle shield 1.1 and the guide pin 1.1.3 to advance distally, so that the needle shield 1.1 surrounds the hypodermic needle 2.1 of the pre-filled syringe 2 in an advanced position III.

The separating wall 1.2.6 has an axial dimension extending parallel to the central axis A and into the widened section 1.2.5.2 of the guide track 1.2.5. The axial dimension defines a minimal axial distance which the needle shield 1.1 has to be moved with respect to the support body 1.2 before the advanced position III is accessible for the needle shield 1.1 to enter and the safety features preventing the re-use of the safety device 1 are activated. This avoids an unintentional activation of the safety features of the safety device 1, when the needle shield 1.1 is accidentally pushed distally by an axial length that is smaller than the minimal axial distance.

The safety device 1 generates an audible feedback indicating the activation of the safety features. The audible feedback can be generated by the flexible separating wall 1.2.6 snapping back into its rest position substantially parallel to the central axis A when the needle shield 1.1 is moved distally with respect to the support body 1.2 by an axial length that exceeds the minimal axial distance.

Before the medication is expelled through the hypodermic needle 2.1, the needle shield 1.1 is moved further in the proximal direction until it reaches the retracted position III illustrated in FIG. 3, whereby the guide pin 1.1.3 is retained within the guide track 1.2.5 in the intermediate position PII. The compression spring 1.4 is fully compressed and fully charged. The hypodermic needle 2.1 penetrates the skin of the patient, so that the medication contained in the inner cavity 2.3.1 can be injected in the following second stage of the injection.

Throughout the first stage of the injection, the outward projection 1.2.3 is retained in the first section 1.3.2.1 of the longitudinal recess 1.3.2, whereby a distal movement of the outer body 1.3 with respect to the support body 1.2 is prevented. When the guide pin 1.1.3 reaches the intermediate position PII and the needle shield 1.1 enters the corresponding retracted position II, the outward projection 1.2.3 deflects in the radial inward direction, leaves the first section 1.3.2.1 and enters the second section 1.3.2.2 of the longitudinal recess 1.3.2, so that the outer body 1.3 is allowed to move relative to the support body 1.2 in the second stage of the injection.

In the second stage, the outer body 1.3 moves with respect to the support body 1.1 in the distal direction. Simultaneously, the piston rod 2.5 interacting with the outer body 1.3 is actuated to move the piston 2.4 in the distal direction, whereby the medication contained in the inner cavity 2.3.1 is delivered through the hypodermic needle 2.1 and beneath the skin of the patient.

At the end of the injection stroke, the inwardly protruding locking catch 1.3.4.1 formed to the clamp arm 1.3.4 latches to the corresponding locking recess 1.2.4 formed into the support body 1.2 to irreversibly lock the support body 1.2 with respect to the outer body 1.3.

Figure 6E:
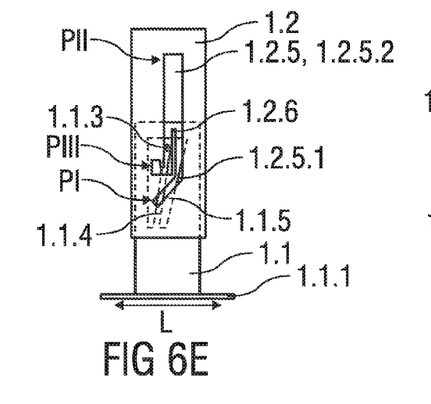

The injection device D comprising the safety device 1 with the pre-filled syringe 2 received therein is removed from the skin surface. The needle shield 1.1 immediately moves distally towards the advanced position PIII by the action of the relaxing compression spring 1.4. As indicated in FIG. 6E, the guide pin 1.1.3 jointly moves with the needle shield 1.1 distally, whereby the guide pin 1.1.3 is guided by the separating wall 1.2.6 towards the end position PIII.

Figure 6F:
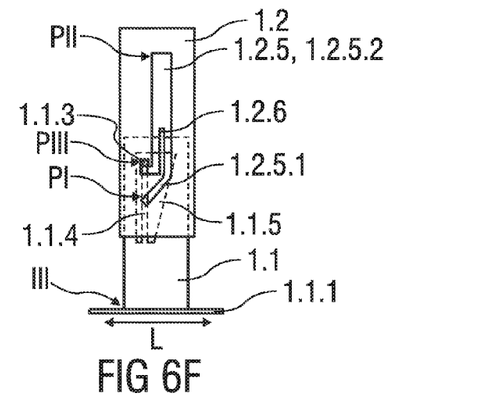

As indicated in FIG. 6F, the guide pin 1.1.3 enters the U-shaped indent defining the end position PIII of the guide track 1.2.5, whereby the flexible arm 1.1.4 relaxes to move the guide pin 1.1.3 laterally towards the end position PIII.

The guide pin 1.1.3 is firmly retained in the end position PIII, as the guide pin 1.1.3 abuts the U-shaped indent in the distal and in the lateral direction. The flexible arm 1.1.4 is in the rest position, so that the guide pin 1.1.3 is laterally non-biased in the end position PIII. A lateral movement of the guide pin 1.1.3 is prevented by the form of the U-shaped indent of the guide track 1.2.5 at the end position PIII and by the flexible arm 1.1.4. Thus, the guide pin 1.1.3 in the end position PIII irreversibly locks the needle shield 1.1 into the advanced position III after a single use of the safety device 1.

In one embodiment of the invention, the hypodermic needle 2.1 is hidden from the view of the patient throughout the injection.

Figure 7:
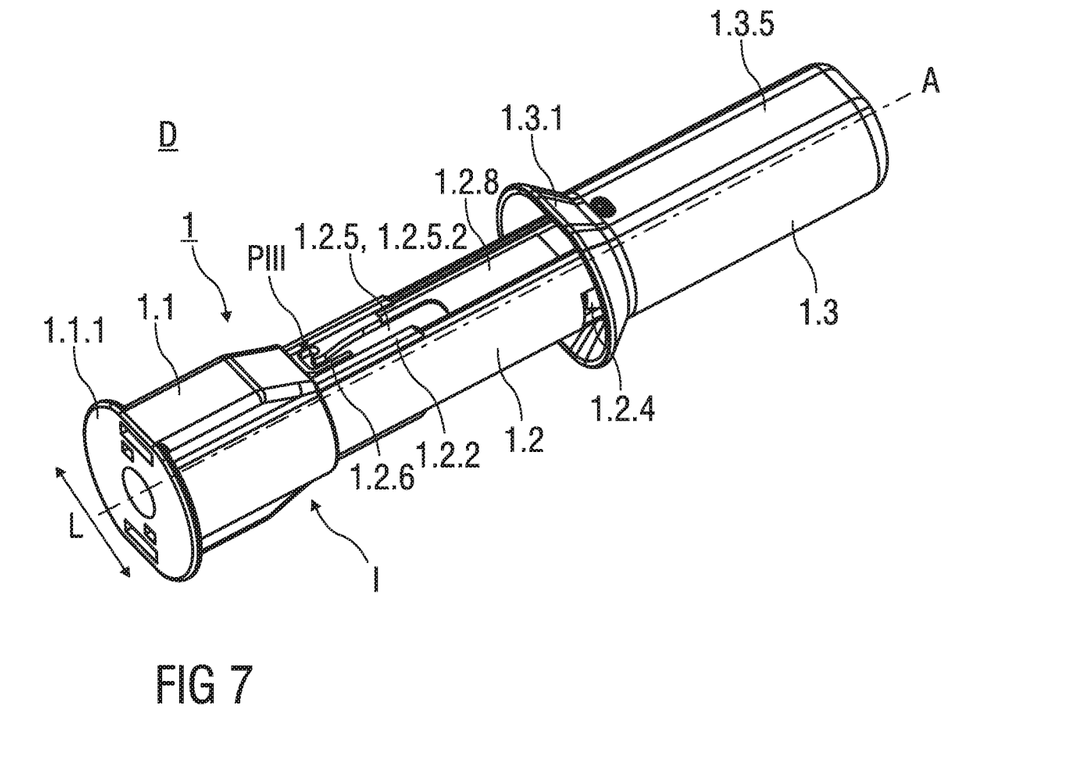
FIG. 7 shows a perspective view of the injection device according to a second embodiment of the invention prior to use comprising a safety device and a pre-filled syringe.

FIG. 7 shows a perspective view of the injection device D according to a second embodiment. The safety device 1 of the injection device D comprises a hollow support body 1.2 with two substantial planar sides 1.2.8 that are arranged opposite to each other. One guide track 1.2.5 is formed into an outer surface of each of the two substantial planar sides 1.2.8. The guide track 1.2.5 according to the second embodiment has the shape of a recess and does not completely pass through the planar side 1.2.8.

The needle shield 1.1 has an opening at a proximal end that comprises a contour that corresponds to a cross-section of the support body 1.2 with the two substantially planar sides 1.2.8. The needle shield 1.1 is sized to substantially receive the support body 1.2. The support body 1.2 slides into the needle shield 1.1 when the needle shield 1.1 is moved from the initial position I to the retracted position II.

The flexible arm 1.1.4 is arranged within the hollow needle shield 1.1 in a way that the flexible arm 1.1.4 is inaccessible from the outside. A distal end of the flexible arm 1.1.4 is connected to a distal end of the needle shield 1.1. The flexible arm 1.1.4 extends in its unbiased position essentially parallel to the central axis A. The guide pin 1.1.3 protrudes from the proximal end of the flexible arm 1.1.4 in a radial inward direction and into the guide track 1.2.5. The flexible arm 1.1.4 is connected to the needle shield 1.1 in a way that allows for a substantial planar movement of the guide pin 1.1.3 when the flexible arm 1.1.4 is deflected during the use of the injection device D. During the injection, the guide pin 1.1.3 moves within and along the guide track 1.2.5 formed into the substantial planar side 1.2.8 of the support body 1.2.

The proximal end of the support body 1.2 is received within the open distal end of the outer body 1.3, whereas the outer body 1.3 is slidable with respect to the support body 1.2 in a distal direction to substantially receive the support body 1.2 inside the outer body 1.3. The outer body 1.3 has a shape that corresponds to the shape of the support body 1.2 and comprises two substantially planar outer sides 1.3.5 opposing the two substantially planar sides 1.2.8 of the support body 1.2.

The circumferential and outwardly protruding hand flange 1.3.1 is integrally formed to an outer surface of the outer body 1.3 close to its distal end.

The skin-contact surface 1.1.1 of the needle shield 1.1 is adapted to be pressed against the skin of a patient. The skin-contact surface 1.1.1 provides, apart from the central opening of a size that corresponds to an outer diameter of the needle cap 2.2 of the pre-filled syringe 2 retained within the safety device 1, a closure of the distal end of the substantial hollow needle shield 1.1.

Two diametrical opposing second longitudinal tongues 1.2.2 are formed to the outer surface of each planar side 1.2.8. The second longitudinal tongues 1.2.2 are located adjacent to each guide track 1.2.5 and extend over an axial length of the support body 1.2 and parallel to the central axis A. Each second longitudinal tongue 1.2.2 is received in a correspondingly shaped groove (not illustrated) formed into an inner surface of the needle shield 1.1 when the needle shield 1.1 is moved with respect to the support body 1.2 from the initial position I to the retracted position II. This prevents a jamming of the support body 1.2 and the needle shield 1.1 when these parts 1.2, 1.1 are moved relative to each other.

Furthermore, the longitudinal tongues 1.2.2 also act a secondary depth stop to prevent the outer body 1.3 from moving to far in the distal direction.

The separating wall 1.2.6 is formed to the outer surface of the planar side 1.2.8 of the support body 1.2. The separating wall 1.2.6 extends into the widened section 1.2.5.2 of the guide track 1.2.5 and parallel to the central axis A.

The separating wall 1.2.6 according to the second embodiment shown in FIG. 7 is not deflectable and remains static throughout the use of the injection device D.

Figure 8:
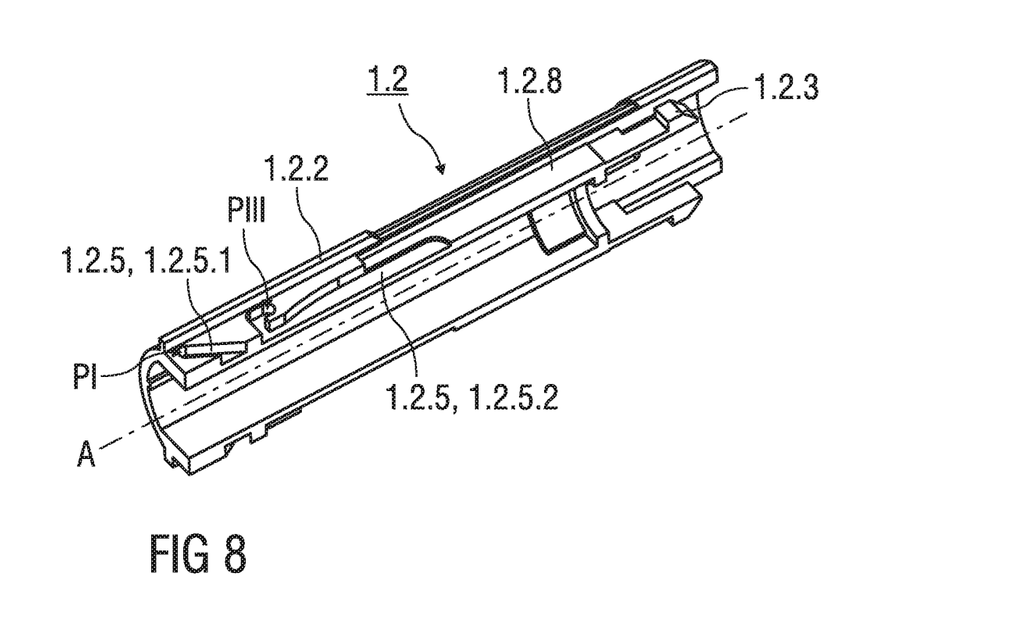
FIG. 8 shows a perspective view of a support body according to the second embodiment that is cut open parallel a central axis for illustrative purposes.

FIG. 8 shows a perspective view of the support body 1.2 according to the second embodiment that is cut open parallel the central axis A for illustrative purposes. The guide track 1.2.5 has the form of a recess, so that an interior of the support body 1.2 is inaccessible from the outside. The outward projection 1.2.3 is received in the longitudinal locking recess 1.3.2 formed into an inner surface of the outer body 1.3.

FIGS. 9A to 9E show details of the guide track 1.2.5 formed into the support body 1.2 and the movement of the guide pin 1.1.3 within the guide track 1.2.5 according to the second embodiment during the injection. FIGS. 9A to 9E illustrate the movement of the guide pin 1.1.3 within the guide track 1.2.5 according to the second embodiment, whereby the separating wall 1.2.6 remains static throughout the injection.

Figure 9A:
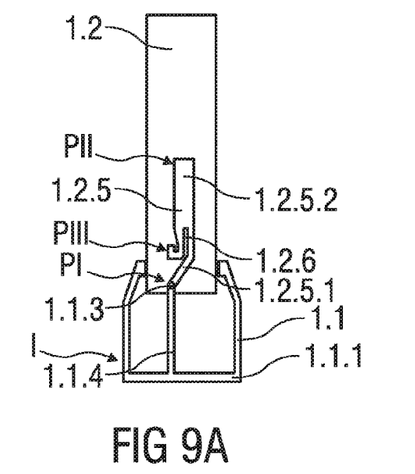
FIG. 9A to 9E show details of a guide track and the movement of a guide pin within the guide track during use of the safety device according to the second embodiment of the invention.

As shown in FIG. 9A, the guide pin 1.1.3 is retained prior to the injection in the start position PI at the distal end of the inclined section 1.2.5.1 of the guide track 1.2.5, affixing the needle shield 1.1 to the initial position I. In the initial position I, the hypodermic needle 2.1 is surrounded by the needle shield 1.1.

The injection is carried out by orientating the central axis A essentially perpendicular to the skin of the patient, whereas the skin-contact surface 1.1.1 of the needle shield 1.1 rests on the skin surface of the patient and the proximal section of the outer body 1.3 proximal of the hand flange 1.3.1 is gripped by the user performing the injection. The hand flange 1.3.1 supports the hand of the user to carry out an injection stroke, whereby the outer body 1.3 is distally moved towards the skin surface of the patient to initiate the injection.

Figure 9B:
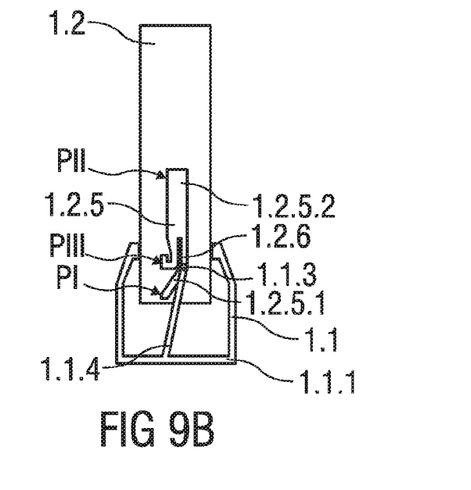

The injection is carried out in stages. In a first stage, the support body 1.2 is pushed inside the needle shield 1.1 in the distal direction against the biasing force of the compression spring 1.4. As illustrated in FIG. 9 B, the guide pin 1.1.3 leaves its start position PI and moves along the inclined section 1.2.5.1 of the guide track 1.2.5. As the distal end inclined section 1.2.5.1 is oriented at an acute angle relative to the central axis A, the movement of the guide pin 1.1.3 causes the flexible arm 1.1.4 to become laterally deflected and stressed, so that the guide pin 1.1.3 is biased in a lateral direction.

The guide pin 1.1.3 abuts the separating wall 1.2.6 in the lateral direction. The separating wall 1.2.6 remains static and guides the guide pin 1.1.3 further in the proximal direction.

The separating wall 1.2.6 prevents the guide pin 1.1.3 from entering the end position PIII as the guide pin 1.1.3 enters the widened section 1.2.5.2 from the start position PI.

Figure 9C:
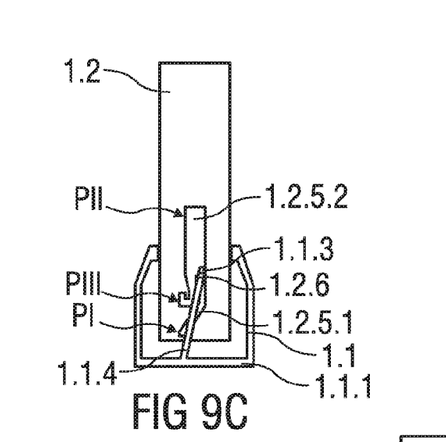
Figure 9D:
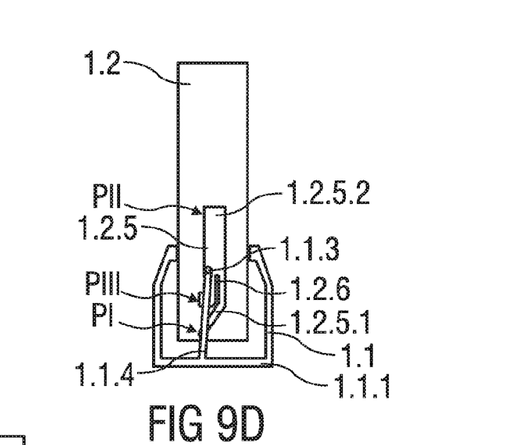

The guide pin 1.1.3 moves further proximally towards an intermediate position PII and reaches the proximal end of the separating wall 1.2.6, as illustrated in FIG. 9C. The biased guide pin 1.1.3 passes the separating wall 1.2.6 in the lateral direction L, as indicated in FIG. 9D, whereby the deflected and energized flexible arm 1.1.4 at least partially relaxes.

At this point, the safety features of the safety device 1 that in particular prevent a re-use of the injection device D are activated, as the end position PIII is accessible for the guide pin 1.1.3 to enter whereas the guide pin 1.1.3 is prevented to re-enter the start position PI.

Before the medication is expelled through the hypodermic needle 2.1, the needle shield 1.1 is moved further in the proximal direction until it reaches the retracted position III illustrated in FIG. 3, whereby the guide pin 1.1.3 is retained within the guide track 1.2.5 in the intermediate position PII. The compression spring 1.4 is fully compressed and fully charged. The hypodermic needle 2.1 penetrates the skin of the patient, so that the medication contained in the inner cavity 2.3.1 can be injected in the following second stage of the injection.

In the second stage, the outer body 1.3 moves with respect to the support body 1.2 in the distal direction. Simultaneously, the piston rod 2.5 interacting with the outer body 1.3 is actuated to move the piston 2.4 in the distal direction, whereby the medication contained in the inner cavity 2.3.1 is delivered through the hypodermic needle 2.1 and beneath the skin of the patient.

Figure 9E:
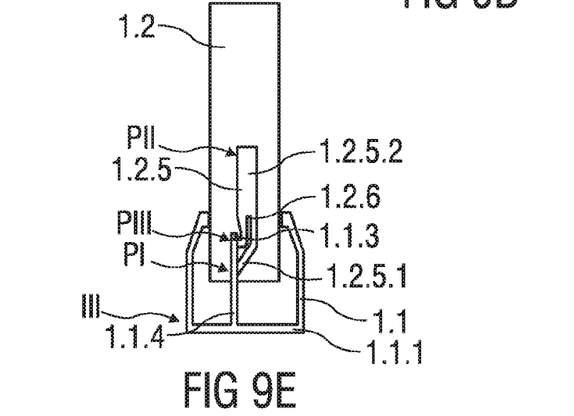

A subsequent removal of the safety device 1 causes the needle shield 1.1 and the guide pin 1.1.3 to advance distally, so that the needle shield 1.1 surrounds the hypodermic needle 2.1 of the pre-filled syringe in an advanced position III. FIG. 9E shows the needle shield 1.1 firmly retained in the advanced position III by the guide pin 1.1.3 being retained in the U-shaped indent of the guide track 1.2.5 defining the end position PIII, whereby a re-usage of the injection and/or the safety device 1 is prevented.

The safety device 1 presented herein provides a simple mechanism to avoid needle stick injuries. The injection is carried out by a simple linear movement of the outer body 1.3 towards the skin of the patient, whereby the safety features, that provide needle safety and prevent re-usage of the safety device 1, are automatically activated.

The invention claimed is:

1. A safety device for a pre-filled syringe comprising:
    a hollow support body for mounting the pre-filled syringe therein, the pre-filled syringe comprising a hypodermic needle attached to a distal end of the pre-filled syringe,
    a hollow needle shield that is slidable relative to the support body, the needle shield and the support body being configured such that relative rotation of the support body and the needle shield is inhibited, and
    a guiding mechanism to guide movement of the needle shield relative to the support body, the guiding mechanism comprising:
    a flexible arm,
    a guide pin extending from the flexible arm in a radial direction,
    a guide track, wherein the guide pin protrudes into the guide track, and
    a separating wall that extends into the guide track in a direction parallel to a central axis of the safety device,
    wherein, the guide pin is configured to move along the guide track to deflect the flexible arm in a lateral direction perpendicular to the central axis when the needle shield is slid relative to the support body,
    wherein the guide pin is movable within the guide track from a start position through an intermediate position to an end position such that a distal end of the needle of the pre-filled syringe is surrounded by the needle shield when the guide pin is in the start position and the end position, and
    wherein the flexible arm interacts with the separating wall to guide movement of the guide pin along the guide track.

2. The safety device according to claim 1, wherein the flexible arm is connected to one of the needle shield and the support body, and the guide track is formed into the other of the needle shield and the support body.

3. The safety device according to claim 1, wherein the separating wall extends into a widened section of the guide track that extends parallel to the central axis of the safety device.

4. The safety device according to claim 1, wherein the separating wall has an axial dimension extending parallel to the central axis that defines substantially a minimal axial distance that the needle shield has to be moved with respect to the support body until the safety device is prevented from re-usage.

5. The safety device according to claim 1, wherein an audible feedback is generated when the needle shield is retracted with respect to the support body by a distance that matches or exceeds a minimal axial distance.

6. The safety device according to claim 1, wherein the separating wall prevents the guide pin from accessing an end position within the guide track from one of a distal direction and a proximal direction, whereas guide pin is allowed to enter the end position from the other of the distal direction and the proximal direction.

7. The safety device according to claim 1, wherein the guide track is formed into a surface of the support body or into a surface of the needle shield as a recess.

8. The safety device according to claim 1, wherein the guide track forms an aperture in one of the needle shield or the support body.

9. The safety device according to claim 8, wherein the separating wall is flexible and the guide pin moves along the guide track to deflect the separating wall, whereby the deflection of the flexible separating wall depends on the deflection of the flexible arm.

10. The safety device according to claim 8, wherein an elasticity of the separating wall is adapted to an elasticity of the flexible arm, so that the separating wall is deflectable by the deflected flexible arm.

11. The safety device according to claim 1, wherein the guide pin is biased in the lateral direction by the deflected flexible arm.

12. The safety device according to claim 1, wherein the flexible arm in a rest position extends essentially parallel to the central axis, the flexible arm being in the rest position when the guide pin is in the start position and the end position.

13. The safety device according to claim 1, wherein the guide track comprises an inclined section oriented at an angle with respect to the central axis.

14. The safety device according to claim 13, wherein the needle shield is retained in an initial position by the guide pin being retained in the start position within the inclined section of the guide track, the needle shield in the initial position protruding the support body in a distal direction, the needle shield is movable from the initial position to a retracted position and further to an advanced position, the needle shield protruding the support body in the initial position and in the advanced position.

15. The safety device according to claim 14, wherein the safety device comprises a compression spring arranged in a non-energized state when the needle shield is in the initial position.

16. The safety device according to claim 1, further comprising a first longitudinal groove and a first longitudinal tongue to inhibit relative rotation of the needle shield and the support body.

17. An injection device comprising:
a pre-filled syringe with a hypodermic needle attached to a distal end of the pre-filled syringe; and a safety device comprising:
a hollow support body for mounting the pre-filled syringe therein such that the hypodermic needle protrudes past a distal end of the support body,
a hollow needle shield that is slidable relative to the support body, the needle shield and the support body being configured such that relative rotation of the support body and the needle shield is inhibited, and
a guiding mechanism to guide movement of the needle shield relative to the support body, the guiding mechanism comprising:
a flexible arm,
a guide pin extending from the flexible arm in a radial direction,
a guide track, wherein the guide pin protrudes into the guide track, and
a separating wall that extends into the guide track in a direction parallel to a central axis of the safety device,
wherein the guide pin is configured to move along the guide track to deflect the flexible arm in a lateral direction perpendicular to the central axis when the needle shield is slid relative to the support body,
wherein the guide pin is movable within the guide track from a start position through an intermediate position to an end position such that a distal end of the needle of the pre-filled syringe is surrounded by the needle shield when the guide pin is in the start position and the end position, and
wherein the flexible arm interacts with the separating wall to guide movement of the guide pin along the guide track.

18. The injection device according to claim 17, wherein the needle shield is movable from an initial position to a retracted position and further to an advanced position, the needle being surrounded by the needle shield in the initial position and in the advanced position and exposed in the retracted position.

19. The injection device according to claim 17, wherein the flexible arm in a rest position extends essentially parallel to the central axis, the flexible arm being in the rest position when the guide pin is in the start position and the end position.

* * * * *